(12) United States Patent
Friedman et al.

(10) Patent No.: US 12,070,618 B2
(45) Date of Patent: Aug. 27, 2024

(54) SYSTEMS AND METHODS FOR PHOTOACTIVATING A PHOTOSENSITIZER APPLIED TO AN EYE

(71) Applicant: Avedro, Inc., Waltham, MA (US)

(72) Inventors: Marc D. Friedman, Needham, MA (US); Mikhail Smirnov, North Andover, MA (US); Pavel Kamaev, Lexington, MA (US)

(73) Assignee: AVEDRO, INC., Waltham, MA (US)

( * ) Notice: Subject to any disclaimer, the term of this patent is extended or adjusted under 35 U.S.C. 154(b) by 78 days.

(21) Appl. No.: 17/521,276

(22) Filed: Nov. 8, 2021

(65) Prior Publication Data

US 2022/0054858 A1 Feb. 24, 2022

Related U.S. Application Data

(63) Continuation of application No. 16/384,099, filed on Apr. 15, 2019, now Pat. No. 11,167,149, which is a
(Continued)

(51) Int. Cl.
*A61N 5/06* (2006.01)
*A61F 9/007* (2006.01)
*A61F 9/02* (2006.01)

(52) U.S. Cl.
CPC .......... *A61N 5/0624* (2013.01); *A61F 9/0079* (2013.01); *A61F 9/029* (2013.01);
(Continued)

(58) Field of Classification Search
CPC ........ A61N 5/06; A61N 5/0613; A61N 5/062; A61N 5/0622; A61N 5/0624;
(Continued)

(56) References Cited

U.S. PATENT DOCUMENTS 3,169,459 A 2/1965 Friedberg et al.
4,034,750 A 7/1977 Seiderman
(Continued)

FOREIGN PATENT DOCUMENTS

DE 102008046834 3/2010
EP 1285679 2/2003
(Continued)

OTHER PUBLICATIONS

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164.
(Continued)

*Primary Examiner* — Ahmed M Farah
(74) *Attorney, Agent, or Firm* — K&L Gates LLP

(57) ABSTRACT

An antimicrobial treatment system comprises a wearable photoactivation device. The wearable photoactivation device includes a body configured to be positioned on a head of a subject over one or more eyes of the subject. The body includes one or more windows or openings that allow the one or more eyes to see through the body. The body includes one or more photoactivating light sources coupled to the body and configured to direct photoactivating light to the one or more eyes according to illumination parameters. The illumination parameters determine a dose of the photoactivating light that activates, according to photochemical kinetic reactions, a photosensitizer applied to the one or more eyes and generates reactive oxygen species that provide an antimicrobial effect in the one or more eyes, without substantially inducing cross-linking activity that produces biomechanical changes in the one or more eyes.

14 Claims, 5 Drawing Sheets

Related U.S. Application Data continuation of application No. 15/137,748, filed on Apr. 25, 2016, now Pat. No. 10,258,809.

(60) Provisional application No. 62/279,951, filed on Jan. 18, 2016, provisional application No. 62/152,568, filed on Apr. 24, 2015, provisional application No. 62/152,533, filed on Apr. 24, 2015.

(52) U.S. Cl.
CPC ..... *A61N 5/062* (2013.01); *A61M 2202/0208* (2013.01); *A61M 2205/3368* (2013.01); *A61M 2205/36* (2013.01); *A61M 2205/52* (2013.01); *A61M 2210/0612* (2013.01); *A61N 2005/0626* (2013.01); *A61N 2005/0648* (2013.01); *A61N 2005/0661* (2013.01)

(58) Field of Classification Search
CPC .... A61N 2005/0626; A61N 2005/0627; A61N 2005/0632; A61N 2005/0643; A61N 2005/0648; A61N 2005/0645; A61N 2005/0647; A61N 2005/065; A61N 2005/0651; A61N 2005/0652; A61N 2005/10626; A61N 2005/0661; A61F 9/0008; A61F 9/0017; A61F 9/0026; A61F 9/0079; A61M 2202/02; A61M 2202/0208; A61M 2202/0216; A61M 2205/3368; A61M 2205/36
USPC ................................ 607/88–91, 94
See application file for complete search history.

(56) References Cited

U.S. PATENT DOCUMENTS

| | | | |
|---|---|---|---|
| 4,161,013 A | 7/1979 | Grodzinsky et al. |
| 4,326,529 A | 4/1982 | Doss et al. |
| 4,381,007 A | 4/1983 | Doss |
| 4,665,913 A | 5/1987 | L'Esperance, Jr. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,098,426 A | 3/1992 | Sklar et al. |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,450,144 A | 9/1995 | Ben Nun |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,608,472 A | 3/1997 | Szirth et al. |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,443,978 B1* | 9/2002 | Zharov ............... A61N 5/0616 606/2 |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Chicaning, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,237,898 B1 | 7/2007 | Hohla et al. |
| 7,270,658 B2 | 9/2007 | Woloszko et al. |
| 7,302,189 B2 | 11/2007 | Kawahata |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,871,378 B1 | 1/2011 | Chou et al. |
| 7,898,656 B2 | 3/2011 | Yun et al. |
| 7,935,058 B2 | 5/2011 | Dupps, Jr. et al. |
| 7,981,097 B2 | 7/2011 | Paoli, Jr. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 8,574,277 B2 | 11/2013 | Muller et al. |
| 8,715,273 B2 | 5/2014 | Thyzel |
| 8,995,618 B2 | 3/2015 | Gertner |
| 9,005,261 B2 | 4/2015 | Brinkmann |
| 10,258,809 B2* | 4/2019 | Friedman ............... A61N 5/062 |
| 10,512,534 B2 | 12/2019 | Tai et al. |
| 11,207,410 B2* | 12/2021 | Kamaev ............... A61P 43/00 |
| 2001/0041856 A1 | 11/2001 | McDaniel |
| 2001/0047012 A1 | 11/2001 | Desantis, Jr. |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0042638 A1 | 4/2002 | Iezzi et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0030908 A1 | 2/2003 | Cheng et al. |
| 2003/0056281 A1 | 3/2003 | Hasegawa |
| 2003/0135122 A1 | 7/2003 | Bambot et al. |
| 2003/0175259 A1 | 9/2003 | Karageozian et al. |
| 2003/0189689 A1 | 10/2003 | Rathjen |
| 2003/0208190 A1 | 11/2003 | Roberts et al. |
| 2003/0216728 A1 | 11/2003 | Stern et al. |
| 2003/0231285 A1 | 12/2003 | Ferguson |
| 2004/0001821 A1 | 1/2004 | Silver et al. |

(56) References Cited

U.S. PATENT DOCUMENTS

| | | |
|---|---|---|
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2004/0254520 A1 | 12/2004 | Porteous et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0187599 A1 | 8/2005 | Sharkey et al. |
| 2005/0271590 A1 | 12/2005 | Schwartz et al. |
| 2006/0058592 A1 | 3/2006 | Bouma et al. |
| 2006/0106371 A1 | 5/2006 | Muhlhoff et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195074 A1 | 8/2006 | Bartoli |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0028928 A1 | 2/2007 | Peyman |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0090153 A1 | 4/2007 | Naito et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203478 A1 | 8/2007 | Herekar |
| 2007/0203547 A1 | 8/2007 | Costello et al. |
| 2007/0244470 A1 | 10/2007 | Barker, Jr. et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0033408 A1 | 2/2008 | Bueler et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1* | 7/2009 | Soltz ................ A61N 5/0624 604/20 |
| 2009/0209954 A1 | 8/2009 | Muller et al. |
| 2009/0234335 A1 | 9/2009 | Yee |
| 2009/0271155 A1 | 10/2009 | Dupps, Jr. et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | de Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Omberg et al. |
| 2010/0210996 A1 | 8/2010 | Peyman |
| 2010/0271593 A1 | 10/2010 | Filar |
| 2010/0286156 A1 | 11/2010 | Pinelli |
| 2010/0317588 A1 | 12/2010 | Shoseyov et al. |
| 2010/0318017 A1 | 12/2010 | Lewis et al. |
| 2011/0044902 A1 | 2/2011 | Weiner et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0125076 A1 | 5/2011 | Kraft et al. |
| 2011/0152219 A1 | 6/2011 | Stagni |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1 | 4/2012 | Rubinfeld et al. |
| 2012/0140238 A1 | 6/2012 | Horn et al. |
| 2012/0203051 A1 | 8/2012 | Brooks et al. |
| 2012/0203161 A1* | 8/2012 | Herekar ................ A61P 27/02 604/20 |
| 2012/0209051 A1 | 8/2012 | Blumenkranz et al. |
| 2012/0215155 A1 | 8/2012 | Muller et al. |
| 2012/0283621 A1 | 11/2012 | Muller |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310141 A1* | 12/2012 | Kornfield ............... A61F 9/0008 604/20 |
| 2012/0310223 A1 | 12/2012 | Knox et al. |
| 2012/0327367 A1 | 12/2012 | Anschel |
| 2013/0060187 A1 | 3/2013 | Friedman et al. |
| 2013/0085370 A1 | 4/2013 | Friedman et al. |
| 2013/0116757 A1 | 5/2013 | Russmann |
| 2013/0245536 A1 | 9/2013 | Friedman et al. |
| 2013/0310732 A1 | 11/2013 | Foschini et al. |
| 2013/0338650 A1* | 12/2013 | Jester ................ A61F 9/00825 606/5 |
| 2014/0066835 A1 | 3/2014 | Muller et al. |
| 2014/0194957 A1* | 7/2014 | Rubinfeld ............... A61F 9/013 607/90 |
| 2014/0249509 A1 | 9/2014 | Rubinfeld et al. |
| 2014/0276361 A1 | 9/2014 | Herekar et al. |
| 2014/0277431 A1 | 9/2014 | Herekar et al. |
| 2014/0343480 A1 | 11/2014 | Kamaev et al. |
| 2014/0368793 A1 | 12/2014 | Friedman et al. |
| 2015/0085252 A1 | 3/2015 | Fujimura et al. |
| 2015/0209597 A1* | 7/2015 | Haarlander ............ A61H 23/02 607/90 |
| 2016/0139390 A1 | 5/2016 | Bukshtab et al. |
| 2016/0175442 A1 | 6/2016 | Kamaev et al. |
| 2016/0310758 A1 | 10/2016 | Friedman et al. |
| 2016/0317833 A1* | 11/2016 | Tedford ................ A61N 5/0622 |
| 2017/0156926 A1 | 6/2017 | Friedman et al. |

FOREIGN PATENT DOCUMENTS

| | | |
|---|---|---|
| EP | 1561440 | 8/2005 |
| EP | 1790383 | 5/2007 |
| EP | 2253321 | 11/2010 |
| IT | MI2010A001236 | 5/2010 |
| JP | 2000/262476 | 9/2000 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |

(56) References Cited

FOREIGN PATENT DOCUMENTS

| | | |
|---|---|---|
| RU | 2456971 | 7/2012 |
| WO | 93/16631 | 9/1993 |
| WO | 94/03134 | 2/1994 |
| WO | 00/74648 | 12/2000 |
| WO | 01/58495 | 8/2001 |
| WO | 03/061696 | 7/2003 |
| WO | 2004/052223 | 6/2004 |
| WO | 2005/110397 | 11/2005 |
| WO | 2006/012947 | 2/2006 |
| WO | 2006/128038 | 11/2006 |
| WO | 2007/001926 | 1/2007 |
| WO | 2007/053826 | 5/2007 |
| WO | 2007/081750 | 7/2007 |
| WO | 2007/120457 | 10/2007 |
| WO | 2007/128581 | 11/2007 |
| WO | 2007/139927 | 12/2007 |
| WO | 2007/143111 | 12/2007 |
| WO | 2008/000478 | 1/2008 |
| WO | 2008/052081 | 5/2008 |
| WO | 2008/095075 | 8/2008 |
| WO | 2009/042159 | 4/2009 |
| WO | 2009/073213 | 6/2009 |
| WO | 2009/114513 | 9/2009 |
| WO | 2009/146151 | 12/2009 |
| WO | 2010/011119 | 1/2010 |
| WO | 2010/015255 | 2/2010 |
| WO | 2010/023705 | 3/2010 |
| WO | 2010/039854 | 4/2010 |
| WO | 2010/093908 | 8/2010 |
| WO | 2011/019940 | 2/2011 |
| WO | 2011/050360 | 4/2011 |
| WO | 2011/116306 | 9/2011 |
| WO | 2012/004726 | 1/2012 |
| WO | 2012/047307 | 4/2012 |
| WO | 2012/149570 | 11/2012 |
| WO | 2012/158991 | 11/2012 |
| WO | 2012/174453 | 12/2012 |
| WO | 2013/062910 | 5/2013 |
| WO | 2013/148713 | 10/2013 |
| WO | 2013/148895 | 10/2013 |
| WO | 2013/149075 | 10/2013 |
| WO | 2014/081875 | 5/2014 |
| WO | 2014/145666 | 9/2014 |
| WO | 2014/202736 | 12/2014 |
| WO | 2016069628 | 5/2016 |

OTHER PUBLICATIONS

Acosta A. et al., "Corneal Stroma Regeneration in Felines After Supradescemetic Keratoprothesis Implantation," Cornea, vol. 25, No. 7, pp. 830-838; Aug. 2006.
Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html.
Baier J. et al., "Singlet Oxygen Generation by UVA Light Exposure of Endogenous Photosensitizers," Biophysical Journal, vol. 91(4), pp. 1452-1459; Aug. 15, 2006.
Ballou, D. et al., "Direct Demonstration Of Superoxide Anion Production During The Oxidation Of Reduced Flavin And Of Its Catalytic Decomposition By Erythrocuprein," Biochemical And Biophysical Research Communications vol. 36, No. 6, pp. 898-904, Jul. 11, 1969.
Barbarino, S. et al., "Post-LASIK ectasia: Stabilization and Effective Management with Riboflavin / ultraviolet A-induced collagen cross-linking," Association for Research in Vision and Ophthalmology, 2006.
Berjano E., et al., "Radio-Frequency Heating of the Cornea: Theoretical Model and In Vitro Experiments," IEEE Transactions on Biomedical Engineering, vol. 49, No. 3, pp. 196-205; Mar. 2002.
Berjano E., et al., "Ring Electrode for Radio-frequency Heating of the Cornea: Modelling and in vitro Experiments," Medical & Biological Engineering & Computing, vol. 41, pp. 630-639; Jun. 2003.

Brüel, A., "Changes In Biomechanical Properties, Composition Of Collagen And Elastin, And Advanced Glycation Endproducts Of The Rat Aorta In Relation To Age," Atherosclerosis 127, Mar. 14, 1996.
Burke, JM et al., Abstract for "Retinal proliferation in response to vitreous hemoglobin or iron", Investigative Ophthalmology & Visual Science, May 1981, 20(5), pp. 582-592.
Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238.
Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008.
Chandonnet, "CO2 Laser Annular Thermokeratoplasty: A Preliminary Study," Lasers in Surgery and Medicine, vol. 12, pp. 264-273; 1992.
Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480.
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011.
Corbett M., et al., "Effect of Collagenase Inhibitors on Corneal Haze after PRK," Exp. Eye Res., vol. 72, Issue 3, pp. 253-259; Jan. 2001.
Coskenseven E. et al., "Comparative Study of Corneal Collagen Cross-linking With Riboflavin and UVA Irradiation in Patients With Keratoconus," Journal of Refractive Surgery, vol. 25, issue 4, pp. 371-376; Apr. 2009.
"DEFINITY (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.brg/web/20100321105500/http://dailymed.nlm.nih.gov/dailymed/drugInfo.cfm?id=8338, on Dec. 14, 2011.
Ehlers W., et al., "Factors Affecting Therapeutic Concentration of Topical Aminocaproic Acid in Traumatic Hyphema," Investigative Ophthalmology & Visual Science, vol. 31, No. 11, pp. 2389-2394; Nov. 1990.
Erskine H., "Avedro Becomes Sponsor of US FDA Clinical Trials of Corneal Collagen Crosslinking," Press Release, Mar. 16, 2010 (1 page).
Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011.
Friedman, M. et al. "Advanced Corneal Cross-Linking System with Fluorescence Dosimetry", Journal of Ophthalmology, vol. 2012, Article ID 303459, dated May 7, 2012.
Frucht-Pery, et al. "Iontophoresis—gentamicin delivery into the rabbit cornea, using a hydrogel delivery probe," Jun. 20, 2003.
Gibson, Q. et al., "The Oxidation Of Reduced Flavin Mononucleotide By Molecular Oxygen," Biochem. J. (1962) 83, 368-377.
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009.
Gravitz L., "Laser Show in the Surgical Suite: Lasers and a century-old dye could supplant needles and thread;" technology review, MIT, Mar./Apr. 2009; retrieved from http://www.technologyreview.com/biomedicine/22088/?lid=1767, on Sep. 26, 2011.
Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009.
Hammer Arthur et al., "Corneal Biomechanical Properties at different Corneal Cross-Linking (CXL) Irradiances," IOVS, May 2014, vol. 55, No. 5, pp. 2881-2884.

(56) References Cited

OTHER PUBLICATIONS

Hitzenberger et al., "Birefringence Properties Of The Human Cornea Measured With Polarization Sensitive Optical Coherence Tomography," Bull. Soc. Beige Ophtalmol., 302, 153-168, 2006.
Holmstrom, B. et al., "Riboflavin As An Electron Donor In Photochemical Reactions," 1867-1871, Nov. 29, 1960.
How to Use DEFINITY: "Frequently Asked Questions;" retrieved from http://www.definityimaging.com/how-faq.html, on Sep. 26, 2011 (3 pages) (date unknown, prior to Apr. 26, 2010).
Imex, "KXL System: Crosslinking Para Cirugia Corneal Bibliografia Cientifica," Product Literature, Nov. 23, 2010.
Kamaev et al., "Photochemical Kinetics Of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Ophthalmology & Visual Science, vol. 51, No. 8, pp. 3929-3934; Aug. 2010.
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UVA-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).
Kissner Anja, et al., "Pharmacological Modification of the Epithelial Permeability by Benzalkonium Chloride in UVA/ Riboflavin Corneal Collagen Cross-Linking," Current Eye Research 35(8), pp. 715-721; Mar. 2010 (7 pages).
Koller, T. et al., "Complication and failure rates after corneal crosslinking," Journal Cataract and refractive surgery, vol. 35, No. 8, Aug. 2009, pp. 1358-1362.
Koller T., et al., "Therapeutische Quervernetzung der Hornhaut mittels UVA und Riboflavin: Therapeutic Cross-Linking of the Cornea Using Riboflavin/UVA," Klinische Monatsblätter für Augenheilkunde, vol. 224, No. 9, pp. 700-706; Sep. 2007 (7 pages).
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).
Krueger, Ronald R., "Rapid VS Standard Collagen CXL with Equivalent Energy Dosing," presentation slides; available at http://www.slideshare.net/logen/krueger-herekar-rapid-cross-linking (date unknown, prior to Nov. 9, 2009) (26 pages).
Massey, V., "Activation Of Molecular Oxygen By Flavins And Flavoproteins," The Journal of Biological Chemistry vol. 269, No. 36, Issue of Sep. 9, pp. 22459-22462, 1994 (4 pages).
Marzouky, et al., Tensioactive-mediated Transepithelial Corneal Cross-linking—First Laboratory Report, European Ophthalmic Review, 2009, 3(2), pp. 67-70.
Lee et al., "Spectrally filtered Raman / Thomson scattering using a rubidium Vapor filter ", AIAA J. 40, pp. 2504-2510 (2002).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Meek, K.M. et al. "The Cornea and Scleera", Collagen: Structure and Mechanics, Chapter 13, pp. 359-396, 2008 (38 pages).
Communication pursuant to Article 94(3) EPC for European Patent Application No. 20207592.5 dated Apr. 13, 2023.

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 bages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
Naoumidi T., et al., "Two-Year Follow-up of Conductive Keratoplasty for the Treatment of Hyperopic Astigmatism," J. Cataract Refract. Surg., vol. 32(5), pp. 732-741; May 2006 (10 pages).
Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
O.V. Shilenskaya et al., "Vtorichnaya katarakta posle implantatsii myagkikh IOL," [online] Aug. 21, 2008 [retrieved Apr. 3, 2013] Retrieved from the Internet: <URL:http://www.reper.ru/rus/index.php?catid=210> (4 pages).
Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).
Pallikaris I., et al., "Long-term Results of Conductive Keratoplasty for low to Moderate Hyperopia," J. Cataract Refract. Surg., vol. 31(8), pp. 1520-1529; Aug. 2005 (10 pages).
Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).
Pinelli R., et al., "C3-Riboflavin Treatments: Where Did We Come From? Where Are We Now?" Cataract & Refractive Surgery Today Europe, Summer 2007, pp. 36-46; Jun. 2007 (10 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli et al., "Tensioactive-mediated Transepithelial Corneal Cross-linking—First Laboratory Report", 2009, European Ophthalmic Review, 3(2), pp. 67-70.
Pinelli R., "The Italian Refractive Surgery Society (SICR) results using C3-R" presented Jun. 22-23, 2007 in Italy (13 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurementand Intrepretation of Brillouin Scattering in the Lens of the Eye," The Royal Society, Abstract only, published 2013 [available online at http:/rspb.royalsocietypublishing.org/content/214/1197/449. short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

(56) References Cited

OTHER PUBLICATIONS

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).
Rolandi et al., "Correlation of Collagen-Linked Fluorescence and Tendon Fiber Breaking Time." Gerontology 1991;27:240-243 (4 pages).
RxList: "Definity Drug Description;" The Internet Drug Index, revised Jun. 16, 2008, retrieved from http://www.rxlist.com/definity-drug.htm, on Sep. 26, 2011 (4 pages).
Saleh et al. "Fundamentals of Photonics" 1991, pp. 74-77.
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Shell, J., "Pharmacokinetics of Topically Applied Ophthalmic Drugs," Survey of Ophthalmology, vol. 26, No. 4, pp. 207-218; Jan.-Feb. 1982 (12 pages).
Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).
Sonoda S., "Gene Transfer to Corneal Epithelium and Keratocytes Mediated by Ultrasound with Microbubbles," Investigative Ophthalmology & Visual Science, vol. 47, No. 2, pp. 558-564; Feb. 2006 (7 pages).
Spoerl E., et al., "Artificial Stiffening of the Cornea by Induction of Intrastromal Cross-links," Der Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Techniques for Stiffening the Cornea," Journal of Refractive Surgery, vol. 15, Issue 6, pp. 711-713; Nov.-Dec. 1999 (4 pages).
Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).
"Tahzib N.G. et al., «Recurrent intraocular inflamation after implantation of the Artiflex phakic intraocular lens for the correction of high myopia,»J Cataract Refract Surg, Aug. 2006; 32(8)1388-91, (abstract) [online] [Retrived Apr. 3, 2013] Retrieved from PubMed, PMID: 16863981".
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thornton, I. et al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.
Thornton et al.(Investigative Ophthalmology and Visual Science, Mar. 2009, vol. 50, No. 3, pp. 1227-1233).
Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).
Tomlinson et al. (Investigative Opthalmology and Visual Science 2006, 47 (10), 4309, 4315.

Trembly et al., "Microwave Thermal Keratoplasty for Myopia: Keratoscopic Evaluation in Porcine Eyes," Journal of Refractive Surgery, vol. 17, No. 6, pp. 682-688; Nov./Dec. 2001 (8 pages).
Turgunbaev N.A. et al. Fotomodifikatsiya sklery u bolnykh s progressiruyuschei blizorukostyu (predvaritelnoe soobschenie). 2010 [online]. Retrieved from the Internet:<URL: http://www.eyepress.ru/article.aspx?7484> (2 pages).
"UV-X: Radiation System for Treatment of Keratokonus," PESCHKE Meditrade GmbH; retrieved from http://www.peschkemed.ch/ on Sep. 27, 2011 (date unknown, prior to Sep. 16, 2008) (1 page).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Wong, J. et al., "Post-Lasik ectasia: PRK following previous stablization and effective management with Riboflavin / ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970) (5 pages).
Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program No. 1073, poster board No. A109.
Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 15, 2011 (pp. 13011-13022).
Zderic V., et al., "Drug Delivery Into the Eye With the Use of Ultrasound," J. Ultrasound Med, vol. 23(10), pp. 1349-1359; Oct. 2004 (11 pages).
Zderic V., et al., "Ultrasound-enhanced Transcorneal Drug Delivery," Cornea vol. 23, No. 8, pp. 804-811; Nov. 2004 (8 pages).
International Preliminary Report on Patentability (IPRP) issued in co-pending International Patent Application No. PCT/US2016/029187, dated Nov. 2, 2017, 6 pages.

* cited by examiner

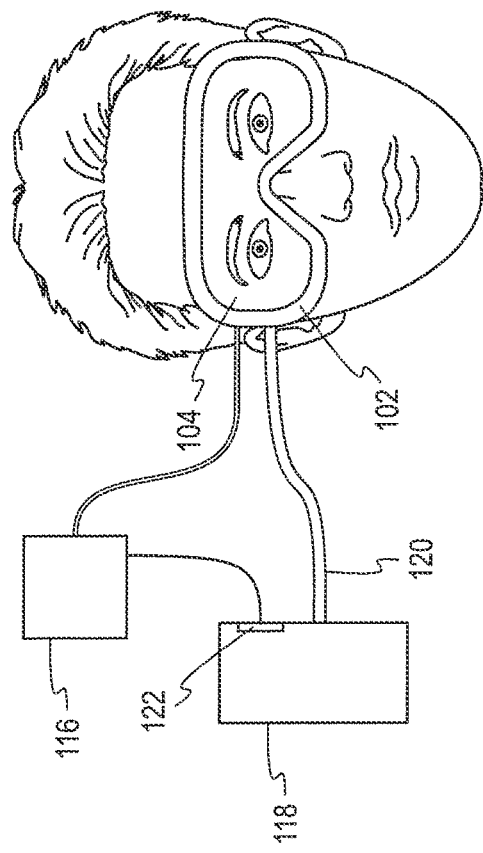
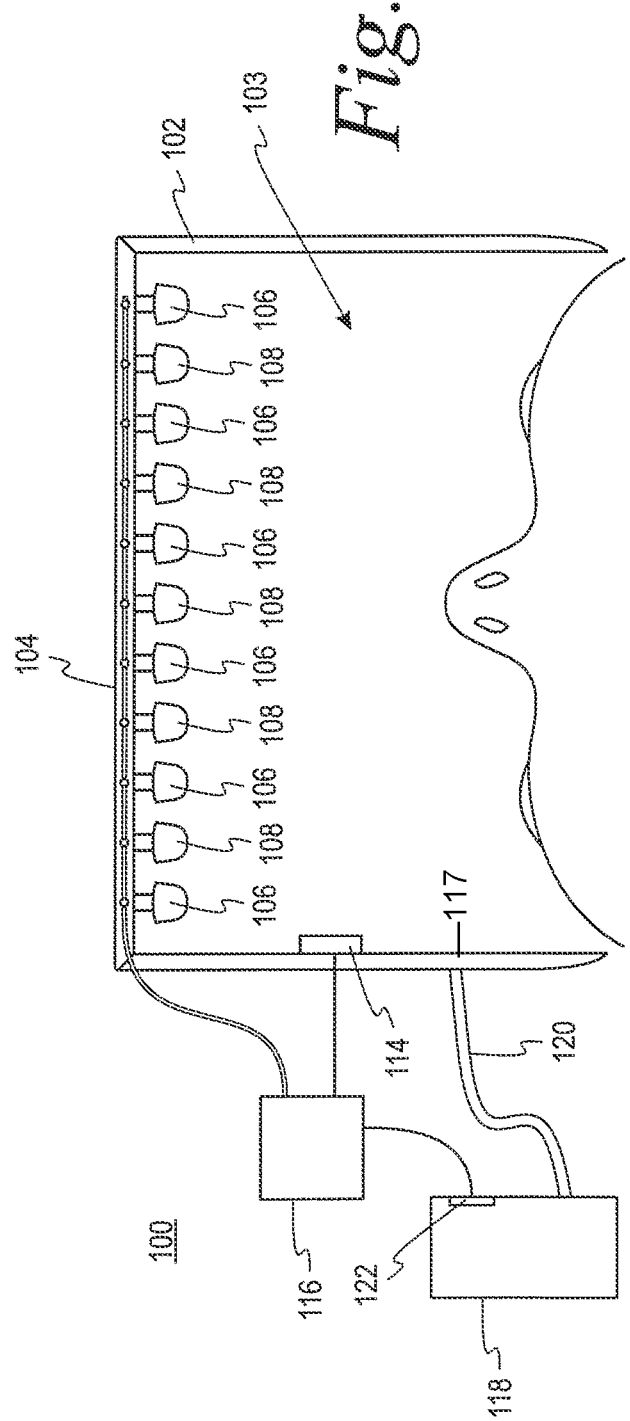

SYSTEMS AND METHODS FOR PHOTOACTIVATING A PHOTOSENSITIZER APPLIED TO AN EYE

CROSS-REFERENCE TO RELATED APPLICATIONS

This application is a continuation of U.S. patent application Ser. No. 16/384,099, filed Apr. 15, 2019, which is a continuation of U.S. patent application Ser. No. 15/137,748, filed Apr. 25, 2016, which claims the benefit of, and priority to, U.S. Provisional Patent Application No. 62/152,568, filed Apr. 24, 2015, U.S. Provisional Patent Application No. 62/152,533, filed Apr. 24, 2015, and U.S. Provisional Patent Application No. 62/279,951, filed Jan. 18, 2016, the contents of these applications being incorporated entirely herein by reference.

BACKGROUND OF THE INVENTION

Field of the Invention

The present disclosure pertains to systems and methods for treating an eye, and more particularly, to systems and methods for activating a photosensitizer applied to an eye during a treatment.

Description of Related Art

Bacterial keratitis is an infection of the cornea caused by bacteria, such as *Staphylococcus Aureus* and *Pseudomonas Aeruginosa*. Amoebic keratitis is an infection of the cornea caused by amoeba, such as *Acanthamoeba*. Fungal keratitis is an infection of the cornea caused by fungi. Such eye infections may cause pain, reduced vision, light sensitivity, and tearing or discharge. If left untreated, these eye infections can cause blindness. Superficial keratitis involves the uppermost layers of the cornea, and after healing, usually leaves no scar on the cornea. On the other hand, deep keratitis affects deeper corneal layers, and after healing, may leave a scar that can affect vision depending on where the scar is located. The treatment of these eye infections may involve the application of an antimicrobial agent to the infected eyes.

SUMMARY

Some antimicrobial treatments employ photosensitizers to sterilize tissues. In general, when photosensitizers are applied to tissue and exposed to photoactivating illumination, resulting photochemical kinetic reactions can produce antimicrobial agents that place microbes in the tissue under stress and induce an apoptotic or necrotic response in the microbes.

Example antimicrobial treatments may, for instance, employ formulations including various concentrations of riboflavin as a photosensitizer. After a riboflavin formulation is applied to tissue, illumination of the tissue with ultraviolet A (UVA) light in particular results in photochemical kinetic reactions that provide an antimicrobial effect.

According to an example embodiment, an antimicrobial treatment system comprises a wearable photoactivation device. The wearable photoactivation device includes a body that defines a chamber shaped to be positioned over and enclose one or more eyes of a subject. The body includes one or more windows that allow the one or more eyes to see through the body. The wearable photoactivation device includes one or more photoactivating light sources coupled to the body and configured to direct photoactivating light to the one or more eyes according to illumination parameters. The illumination parameters determine a dose of the photoactivating light that activates, according to photochemical kinetic reactions, a photosensitizer applied to the one or more eyes and generates reactive oxygen species that provide an antimicrobial effect in the one or more eyes. The wearable photoactivation device includes an inlet configured to couple the body to an oxygen source. The chamber receives oxygen from the oxygen source via the inlet to modify oxygen conditions in the chamber. The activation of the photosensitizer depends on the oxygen conditions.

The wearable photoactivation device may further include one or more heating elements coupled to the body and configured to generate heat in the chamber according to temperature parameters. The temperature parameters modify, according to photochemical kinetic reactions, the activation of the photosensitizer applied to the one or more eyes and the generation of reactive oxygen species that provide the antimicrobial effect in the one or more eyes.

According to another example embodiment, a wearable antimicrobial treatment device includes a body shaped to be positioned on a head of a subject over one or more eyes. The body includes one or more openings that allow the one or more eyes to see through the body. The wearable antimicrobial treatment device includes one or more photoactivating light sources coupled to the body and configured to direct photoactivating light to the one or more eyes according to illumination parameters. The illumination parameters determine a dose of the photoactivating light that activates, according to photochemical kinetic reactions, a photosensitizer applied to the one or more eyes and generates reactive oxygen species that provide an antimicrobial effect in the one or more eyes. The wearable antimicrobial treatment device includes a plurality of guide light sources coupled at a plurality of positions about the body and configured to direct visible light to the one or more eyes from a plurality of directions. The wearable antimicrobial treatment device includes a controller configured to operate the guide light sources to alternately direct the visible light from each direction according to a sequence wherein the subject is directed to look, with the one or more eyes, in each direction according to the sequence and different respective areas of the one or more eyes are exposed to the photoactivating light from the one or more photoactivating light sources.

According to an additional example embodiment, an antimicrobial treatment system comprises a wearable photoactivation device. The wearable photoactivation device includes a body configured to be positioned on a head of a subject over one or more eyes of the subject. The body includes one or more windows or openings that allow the one or more eyes to see through the body. The body includes one or more photoactivating light sources coupled to the body and configured to direct photoactivating light to the one or more eyes according to illumination parameters. The illumination parameters determine a dose of the photoactivating light that activates, according to photochemical kinetic reactions, a photosensitizer applied to the one or more eyes and generates reactive oxygen species that provide an antimicrobial effect in the one or more eyes, without substantially inducing cross-linking activity that produces biomechanical changes in the one or more eyes.

BRIEF DESCRIPTION OF THE DRAWINGS

FIG. 1a illustrates a view of an example photoactivation device for photoactivating a photosensitizer in an antimicrobial treatment, according to aspects of the present disclosure.

FIG. 1b illustrates another view of the example photoactivation device of FIG. 1a.

DESCRIPTION

Figure 2:
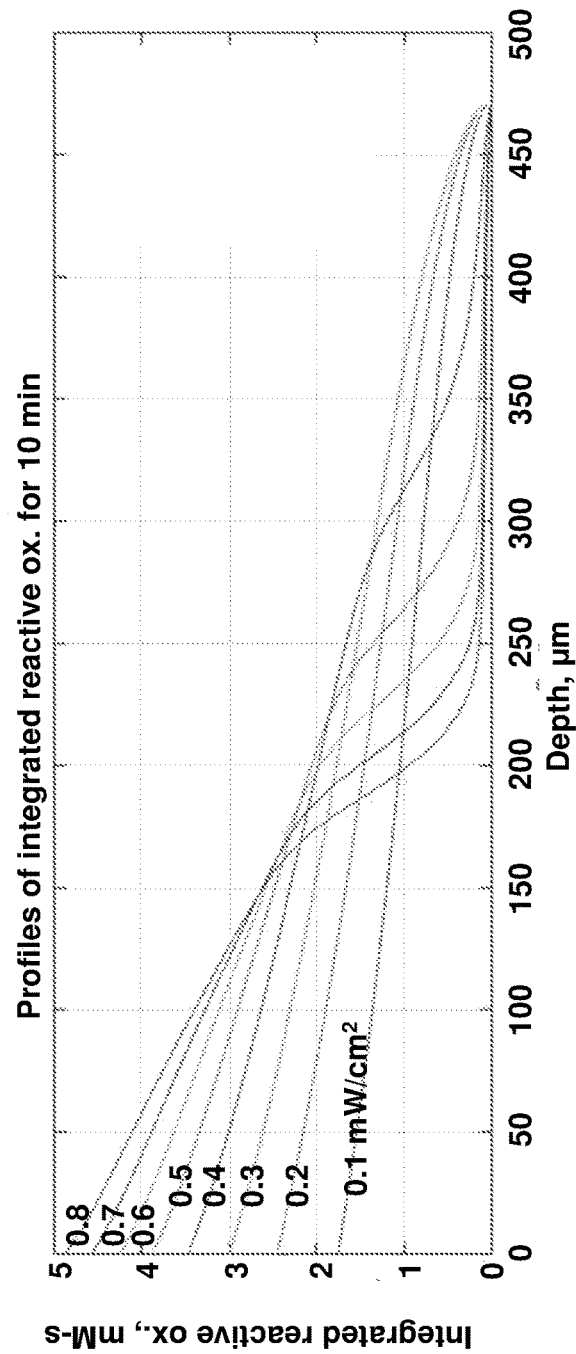
FIG. 2 illustrates a graph of concentration of reactive oxygen species (ROS) generated when various doses of ultraviolet (UV) light are applied to corneas treated with a transepithelial riboflavin formulation, according to aspects of the present disclosure.

Some antimicrobial treatments (also known as antimicrobial photodynamic therapies) employ photosensitizers to sterilize tissues. In general, when photosensitizers are applied to tissue and exposed to photoactivating illumination, resulting photochemical kinetic reactions can produce antimicrobial agents that place microbes in the tissue under stress and induce an apoptotic or necrotic response in the microbes.

Example antimicrobial treatments may, for instance, employ formulations including various concentrations of riboflavin as a photosensitizer. After a riboflavin formulation is applied to tissue, illumination of the tissue with ultraviolet A (UVA) light in particular results in photochemical kinetic reactions that provide an antimicrobial effect.

In particular, the stroma may be treated with riboflavin, and UVA light is delivered to the cornea to activate the riboflavin in the stroma. Upon absorbing UVA radiation, riboflavin undergoes a reaction with oxygen in which reactive oxygen species (ROS) and other radicals are produced. The ROS can provide an antimicrobial effect in the treated tissue.

FIGS. 1a, b illustrate an example photoactivation device 100 that is configured to activate a photosensitizer, such as riboflavin, that has been applied to eye tissue according to an antimicrobial treatment. The photoactivation device 100 combines a plurality of features to enhance or otherwise control photochemical kinetic reactions that produce an antimicrobial effect in the targeted eye tissue. The photoactivation device 100 includes a body 102 that defines a substantially closed chamber 103. As shown in FIGS. 1a, b, the photoactivation device 100 fits over the eyes of a subject in a manner similar to eye goggles and may be coupled more securely to the subject's head with a strap, tape, adhesives, and/or the like. The body 102 includes a window 104 formed from glass, plastic, etc., that allows the subject see through the photoactivation device 100. For instance, the window 104 allows the procedure to be monitored and also allows the subject to read, watch television, or be otherwise occupied during the treatment.

The conditions in the chamber 103 can be controlled and monitored to achieve desired photochemical kinetic reactions and to provide an antimicrobial effect in the targeted eye tissue. The photoactivation device 100 includes photoactivating light sources 106 that emit light (e.g., UVA light) to initiate photochemical kinetic reactions with the photosensitizer that has been applied to the targeted eye tissue. The photoactivating light sources 106 may be light emitting diodes (LED's) that can emit selected wavelengths of light, e.g., 365 nm, 450 nm, etc.

The depth and distribution of the antimicrobial effect may be modulated through a timed increase and/or decrease in temperature in the chamber 103 enclosing the targeted eye tissue. Correspondingly, the photoactivation device 100 includes heating elements 108 that generate heat and increase the temperature within the chamber 103. For instance, the heating elements 108 may include LEDs that can emit electromagnetic energy, such as near-infrared (NIR) light, infrared (IR) light, and/or microwaves, to generate heat. Alternatively or additionally, the heating elements 108 may include resistive heating elements or the like. Furthermore, the temperature of the targeted eye tissue may also be decreased by applying chilled gas, evaporative cooling systems, chilled liquids, etc.

A controller 116 is coupled to the photoactivating light sources 106. The controller 116 can control the photoactivating light sources 106 to apply light with any combination/sequence of pulses or continuous wave having any suitable wavelength, power, irradiance, intensity, duration, duty cycle (for pulses), and/or other illumination parameters.

The controller 116 may also be coupled to the heating elements 108 to control the generation of heat. As shown in FIG. 1b, one or more sensors 114 in the photoactivation device 100 may include temperature sensors (e.g., thermostat, optical sensors, etc.) that monitor the temperature in the chamber 103 and provide feedback for the operation of heating elements 108.

The generation of ROS according to the photochemical kinetic reactions may be highly dependent on the oxygen conditions (e.g., concentration, pressure, etc.) in the targeted eye tissue or the environment around the targeted eye tissue. Correspondingly, the photoactivation device 100 can enhance the antimicrobial effect associated with the ROS by controlling the amount of oxygen available during photoactivation of the photosensitizer. The photoactivation device 100 can increase the partial pressure of oxygen in the chamber 103 that encloses the targeted eye tissue. For instance, the partial pressure of the oxygen may be achieved through the use of hyperoxic addition of oxygen up to 100% and/or through hyperbaric pressurization of up to 2 atm.

As shown in FIGS. 1a, b, the photoactivation device 100 includes an inlet 117 that couples the chamber 103 to an oxygen source 118 via a tube 120. Thus, the oxygen source 118 delivers oxygen gas (e.g., humidified oxygen gas) to the chamber 103 to increase the partial pressure of oxygen. The controller 116 may also be coupled to the oxygen source 118 to control the delivery of oxygen gas to achieve the desired concentration of oxygen in the chamber 103. The one or more sensors 114 may also include oxygen sensors to monitor the concentration of oxygen and provide feedback for the operation of the oxygen source 118.

The treated tissue may be exposed to a sequence of different oxygen conditions to generate different amounts of ROS at different depths in the treated tissue. For instance, example antimicrobial treatments may expose the target tissue to normoxic conditions, followed by hyperoxic conditions, and then followed by hyperbaric conditions.

The oxygen gas in the oxygen source 118 has a temperature that may also be controlled by the controller 116. In particular, the oxygen gas may be kept at a lower temperature that allows the oxygen gas to be used as a cooling agent to control the temperature in the chamber 103. The oxygen source 118 includes one or more sensors 122 that measure the temperature of the oxygen gas and provide feedback to manage the temperature of the oxygen gas.

Accordingly, in combination with the photoactivation device 100, the controller 116 can control various aspects of the antimicrobial treatment applied to the targeted eye tissue and achieve more optimal/efficient antimicrobial effects from the photochemical kinetic reactions. In particular, the controller 116 can modulate: (i) the light from the photoactivating light sources 106; (ii) the heat generated by the heating elements 108; (iii) the concentration of oxygen gas in the chamber 103; and/or (iv) the cooling provided by the oxygen gas. The controller 116 can modulate these aspects of the antimicrobial treatment in any combination and sequence of steps. For example, the controller 116 may initially increase the temperature of the treated tissue by generating heat with the heating elements 108 and, after a certain period of time, may cool the treated tissue by applying cooled oxygen gas from the oxygen source 118.

In some embodiments, the window 104 may include a diffuser to allow other external illumination systems to deliver light additionally or alternatively to the treated tissue. Although not shown, aspects of the controller 116 and/or the oxygen source 118 may be coupled to or otherwise combined with the photoactivation device 100 in a single unit.

The one or more sensors 114, 122 provide feedback for modulating these aspects of the antimicrobial treatment. In some cases, additional monitoring can be provided by additional systems. For example, a fluorescence dosimetry system may be employed to determine the distribution/uptake of the photosensitizer as well as the consumption of the photosensitizer during/after the antimicrobial treatment. An example of a fluorescence dosimetry system is described in U.S. Pat. No. 9,020,580, filed Jun. 4, 2012 and titled "Systems and Methods for Monitoring Time Based Photo Active Agent Delivery or Photo Active Marker Presence," the contents of which are incorporated entirely herein by reference.

The photoactivation device 100 shown in FIGS. 1a, b demonstrates how a device can combine a variety of the features above to enhance or otherwise control photochemical kinetic reactions that produce an antimicrobial effect. Other example embodiments, however, are also contemplated. For instance, photoactivation devices for delivering photoactiving light to corneal tissue are described in U.S. patent application Ser. No. 14/248,966, filed Apr. 9, 2014 and titled "Systems and Methods for Delivering Light in Eye Treatments," the contents of which are incorporated entirely herein by reference. Such photoactivation devices can be modified to include one or more of the features according to aspects of the present disclosure. For example, the devices can be modified to introduce oxygen gas into the environment of the corneal tissue in a manner similar to the photoactivation device 100.

As the outer-most barrier of the cornea, the epithelium functions to regulate nutrients, including oxygen, that are admitted into the stromal tissue from the tear film. This regulation is carried out via the epithelium's physiological "pumps" that are driven by osmotic pressure across the epithelium due to differential concentrations of barrier-permeable solutes on either side of the epithelium. When healthy, certain nutrients in the tear film that become depleted within the stroma can permeate the epithelium via osmotic pressure to resupply the stroma. However, while oxygen and some other small molecule nutrients can reach the stroma according to this mechanism, certain photosensitizers cannot pass through the epithelium.

Riboflavin, for example, is a relatively large, hydrophilic molecule that cannot penetrate the tight junctions of the epithelium. The epithelium slows the amount of riboflavin that can penetrate the stroma. Thus, a variety of approaches have been employed to overcome low riboflavin diffusivity and deliver sufficient concentrations of riboflavin to the stroma for performing treatments. For some corneal treatments, for instance, the epithelium may be removed (epithelium debridement) before a riboflavin solution is applied directly to the stroma. Although removing the epithelium allows riboflavin to reach the stroma, the approach is associated with patient discomfort, risks of infection, and other possible complications. Furthermore, removing the epithelium may be less appropriate for treatments such as antimicrobial treatments.

Meanwhile, other approaches avoid epithelial debridement. For instance, riboflavin may be provided in a transepithelial formulation that allows riboflavin to pass through the epithelium. In particular, some transepithelial formulations include agents, such as benzalkonium chloride (BAC), with a specific osmolarity of sodium chloride (NaCl). Formulations including BAC are described, for example, in U.S. Patent Application Publication No. 2010/0286156, filed on May 6, 2009, and U.S. Patent Application Publication No. 2013/0267528, filed on Jan. 4, 2013, the contents of these applications being incorporated entirely herein by reference. Other transepithelial formulations may employ other additives, such as ethylenediaminetetraacetic acid (EDTA) or tris(hydroxymethyl)aminomethane (Tris).

Yet other transepithelial formulations may employ non-ionic permeability enhancers. Aspects of using transepithelial formulations with such non-ionic agents are further described further in U.S. Provisional Patent Application No. 62/195,144, filed Jul. 21, 2015, U.S. Provisional Patent Application No. 62/255,452, filed Nov. 14, 2015, U.S. Provisional Patent Application No. 62/262,919, filed Dec. 4, 2015, and U.S. Provisional patent Application No. 62/263, 598, filed Dec. 4, 2015, the contents of these applications being incorporated entirely herein by reference.

For instance, such transepithelial formulations employ a non-ionic agent that is chosen using the Hydrophile-Lipophile Balance (HLB) system. The HLB of a permeability enhancer indicates the balance of hydrophilic and lipophilic groups in the molecular structure of the enhancer. Permeability enhancers (or emulsifiers) for the epithelium include a molecule which has both hydrophilic and lipophilic groups. Molecules with HLB number below 9 are considered lipophilic and those above 11 as hydrophilic. Molecules with HLB number between 9 and 11 are intermediate.

For the corneal epithelium, a HLB number that is too great or too small does not help the passage of a photosensitizer through the epithelium. A specific HLB range enhances movement of a photosensitizer through the epithelium. Thus, aspects of the present disclosure employ non-ionic agents that have a hydrophilic/lipophilic balance to achieve optimized diffusivity through the epithelium and the stroma. Advantageously, non-ionic agents are also less corrosive and damaging to the epithelium than ionic agents, such as BAC.

For riboflavin, the HLB range for more effective permeability enhancers has been experimentally determined by the inventors to be between approximately 12.6 and approximately 14.6. A class of permeability enhancers includes various forms of polyethylene glycol (PEG) with different aliphatic chain lengths. According to example embodiments, some riboflavin formulations include specific concentrations of Polidocanol (Polyoxyethylene (9) lauryl ether), which has a HLB number of approximately 13.6.

Some microbes, such as fungi, have dormant phases, while other microbes, such as *Acanthamoeba*, can create cystic cell membrane barriers. Advantageously, additives that enhance permeability can increase penetration and uptake of photosensitizer by microbes and enhance the antimicrobial effect of the photosensitizer.

Additionally or alternatively, another solution and/or mechanical forces may be applied to enhance the permeability of the epithelium and allow the riboflavin to pass more easily through the epithelium. Examples of approaches for enhancing or otherwise controlling the delivery of a photosensitizer to the underlying regions of the cornea are described, for example, in U.S. Patent Application Publication No. 2011/0288466, filed Apr. 13, 2011, and U.S. Patent Application Publication No. 2012/0289886, filed May 18, 2012, the contents of these applications being incorporated entirely herein by reference.

When photosensitizers (e.g., riboflavin) are applied to the cornea, the subsequent application of photoactivating light (e.g., UVA light) may result in cross-linking activity. In particular, the resulting ROS and/or other radicals further interact with the collagen fibrils to induce covalent bonds that bind together amino acids of the collagen fibrils, thereby cross-linking the fibrils. Such cross-linking activity may be desired for treatments that modify biomechanical properties of the cornea, for instance. For antimicrobial treatments, however, it may be more preferable to generate minimal cross-linking activity while providing the deepest and more predictable generation of ROS for their antimicrobial effect.

Example embodiments may employ the transepithelial formulations described above to deliver a photo sensitizer through the epithelium and to desired depths in the corneal tissue. The example embodiments can induce an antimicrobial effect at these depths without inducing cross-linking activity by delivering low doses of photoactivating light that can nevertheless reach these depths and sufficiently generate ROS. In other words, the low doses of photoactivating light minimize cross-linking activity but induce the desired antimicrobial effect. For instance, some implementations may apply UVA light at an irradiance of approximately 0.3 mW/cm$^2$ over an extended amount of time to corneal tissue that has been treated with a transepithelial riboflavin formulation with a non-ionic permeability enhancer, such as Polidocanol.

The presence of microbes can be modeled with a molar concentrator, and the killing efficiency can be represented by the concentration of microbes multiplied by a susceptibility constant for each type of microbe. Additionally, for riboflavin, a model based on the photochemical kinetic reactions described herein may be modified to include an additional molar concentration of microbes. In this manner, the killing efficiency can be calculated and validated by experiment. The total number of photoreactive sites in molar concentration is the sum of two concentrations, microbe molar concentration plus cross-linking site concentration.

By applying a low dose of photoactivating light over an extended amount of time, ROS are generated at desired depths and at rates that allow the whole thickness of the cornea to reach the killing threshold at once while minimizing cross-linking of the anterior cornea.

Figure 3:
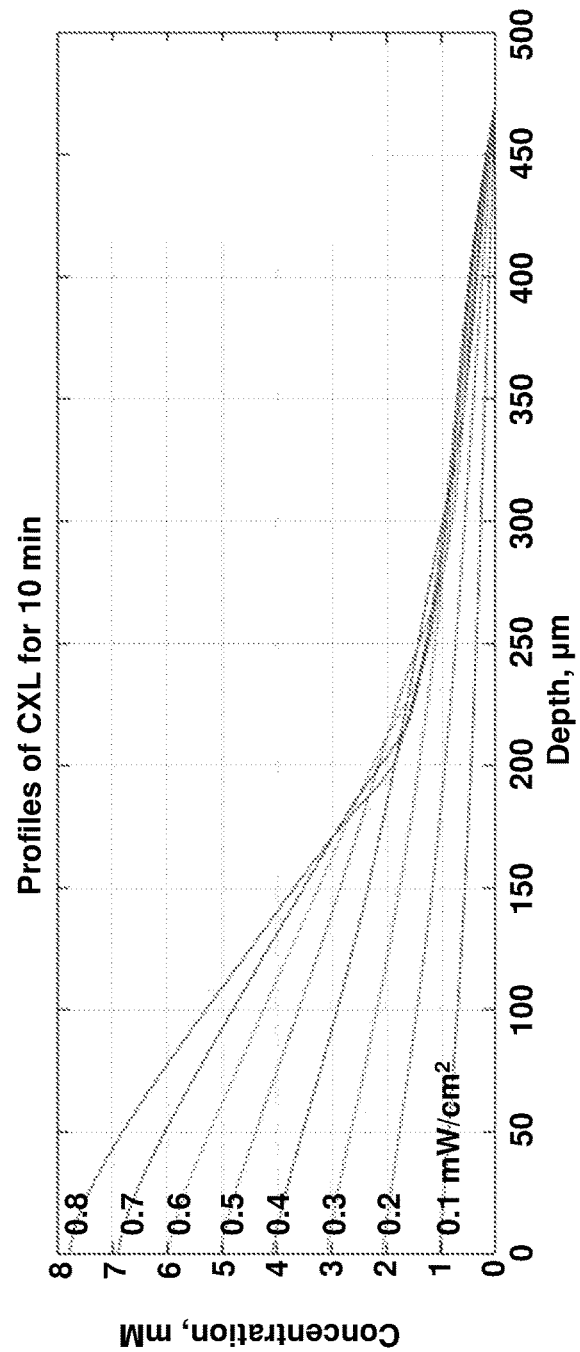
FIG. 3 illustrates, corresponding to FIG. 1, a graph of concentration of cross-links generated when the various doses of UV light are applied to corneas treated with the transepithelial riboflavin formulation, according to aspects of the present disclosure.

FIGS. 2 and 3 illustrate respective graphs of concentrations for ROS and cross-links generated when various doses of UVA light are applied to corneas treated with a transepithelial riboflavin formulation with a non-ionic permeability enhancer as described above. In particular, the doses of UVA light are applied at irradiances of 0.1 mW/cm$^2$, 0.2 mW/cm$^2$, 0.3 mW/cm$^2$, 0.4 mW/cm$^2$, 0.5 mW/cm$^2$, 0.6 mW/cm$^2$, 0.7 mW/cm$^2$, and 0.8 mW/cm$^2$ for 10 minutes. As shown in FIGS. 2 and 3, for instance, the results from an irradiance of 0.3 mW/cm$^2$ are predominately dictated by Beer's law and full oxygen depletion is never achieved for the full stromal thickness as seen with the greater doses. The ROS concentration profile as a function of depth is maintained with the irradiance of 0.3 mW/cm$^2$ but increases with the greater irradiances. Therefore, an antimicrobial threshold can be achieved to a given depth for a given concentration of microbes.

Figure 4:
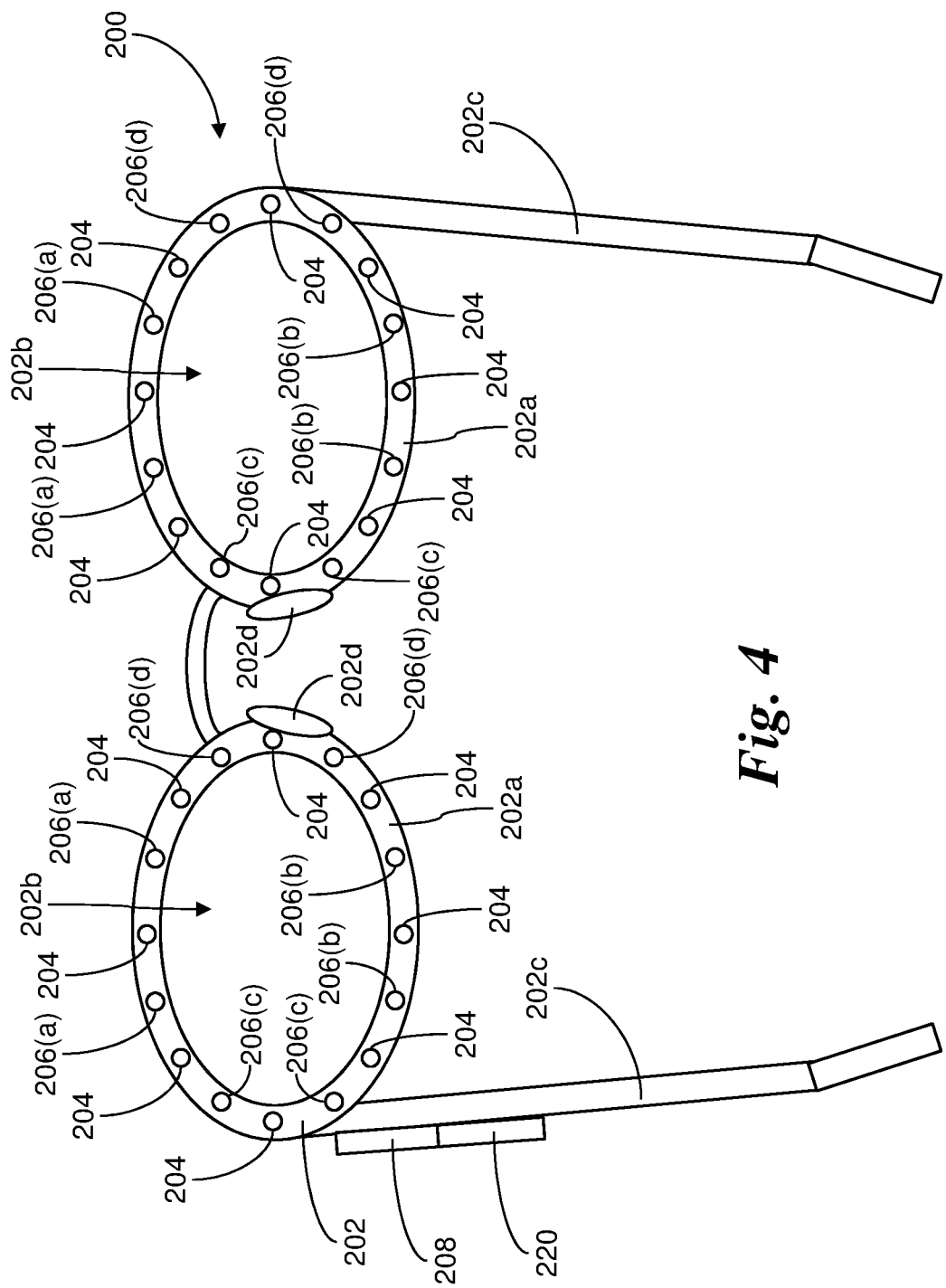
FIG. 4 illustrates another example photoactivation device for photoactivating a photosensitizer in an antimicrobial treatment, according to aspects of the present disclosure.

FIG. 4 illustrates another photoactivation device 200 that is configured to activate a photosensitizer, such as riboflavin, that has been applied to eye tissue according to an antimicrobial treatment. As described above, when photoactivated, the photosensitizer generates ROS that provides an antimicrobial effect. The eye tissue may be treated with a transepithelial formulation with a non-ionic permeability enhancer as described above.

According to one implementation, a medical practitioner, e.g., a nurse, or the patient (once instructed) places drops of the transepithelial photosensitizer formulation every 30 to 60 seconds for a period of approximately 15 to 20 minutes. The transepithelial photosensitizer formulation can be applied to the eyes without the use of specula.

As shown in FIG. 4, the photoactivation device 200 includes a body 202. The body 202 may be shaped and worn like an eyeglasses frame. As such, the body 202 includes rims 202*a* defining openings 202*b* allowing the subject can see through the body 202. The body 202 also includes temples 202*c* and nosepads 202*d* that can support the body 202 on the head of the subject. Although the photoactivation device 200 in FIG. 4 resembles a pair of eyeglasses, it is understood that other shapes and configurations may be employed to situate the photoactivation device 200 stably about the eyes.

The body 202 includes a plurality of photoactivating light sources 204 that can direct photoactivating light to each eye of the subject from the top, bottom, left, and right. In some cases, the photoactivating light sources 204 may include light-emitting diodes (LED's) that direct UVA light simultaneously to eyes that have been treated with a riboflavin formulation. The number of photoactivating light sources 204 may be limited to the number required to provide the desired low dose of photoactivating light, e.g., delivered at an irradiance of approximately 0.3 mW/cm$^2$ for approximately at least 10 minutes.

The body 202 also includes a plurality of guide light sources 206 that emit visible light from above, below, left, and right of each eye. In some cases, the guide light sources 206 may include LEDs. At least one top guide light source 206(*a*) emits light from above each eye; at least one bottom guide light source 206(*b*) emits light from below each eye; at least one left guide light source 206(*c*) emits light from the left of each eye; and at least one right guide light source 206(*d*) emits light from the right of each eye.

A controller 208, e.g., in the form of an electronic/electric chip/circuit, is coupled to the guide light sources 206. The controller 208 can alternately illuminate the guide light sources 206. In particular, the controller 208 may repeatedly, in series: (1) illuminate the top guide light source(s) 206(*a*) for a predetermined period of time (e.g., 10 seconds or other optimal period) while the other guide light sources 206(*b*), (*c*), (*d*) remain off; (2) illuminate the bottom guide light source(s) 206(b) for the predetermined period of time while the other guide light sources 206(a), (c), (d) remain off; (3) illuminate the left guide light source(s) 206(c) for the predetermined period of time while the other guide light sources 206(a), (b), (d) remain off; and (4) illuminate the right guide light source(s) 206(d) for the predetermined period of time while the other guide light sources 206(a), (b), (c) remain off.

Figure 5:
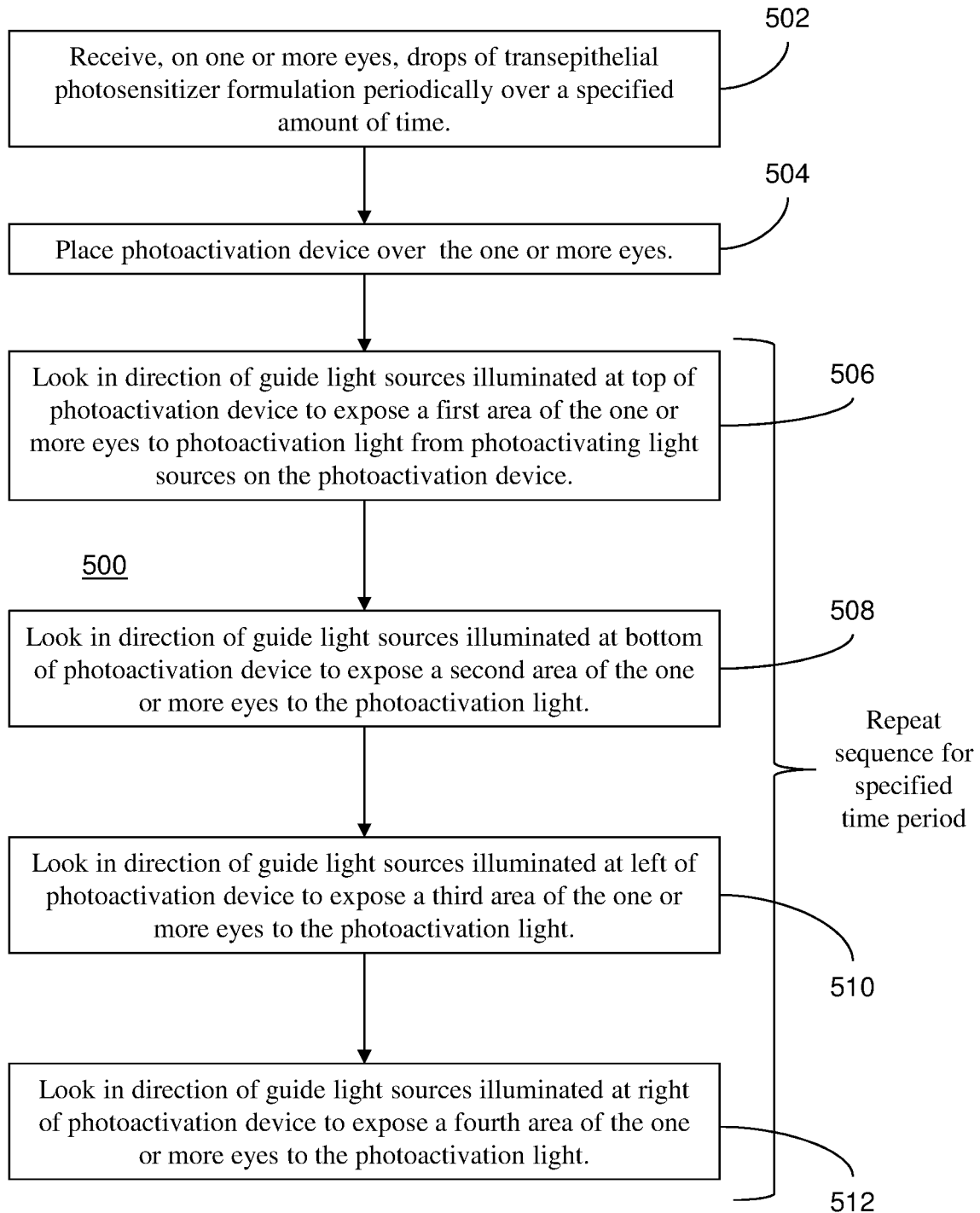
FIG. 5 illustrates an example method for employing the example photoactivation device of FIG. 4, according to aspects of the present disclosure.

FIG. 5 illustrates a method 500 that corresponds to the example above. In step 502, the one or more eyes receive drops of transepithelial photosensitizer formulation periodically over a specified amount of time. In step 504, the photoactivation device 200 is placed over the one or more eyes. In step 506, the one or more eyes look at the guide light sources 206(a) illuminated at the top of the photoactivation device 200 to expose a first area of the one or more eyes to photoactivation light from photoactivating light sources 204 on the photoactivation device 200. In step 508, the one or more eyes look at the guide light sources 206(b) illuminated at the bottom of the photoactivation device 200 to expose the one or more eyes to the photoactivation light. In step 510, the one or more eyes look at the guide light sources 206(c) illuminated at the left of the photoactivation device 200 to expose a third area of the one or more eyes to the photoactivation light. In step 512, the one or more eyes look at the guide light sources 206(d) illuminated at the right of the photoactivation device 200 to expose a fourth area of the one or more eyes to the photoactivation light. In alternative embodiments, the guide light sources 206 may be alternately illuminated in a different sequence. Moreover, the guide light sources 206 may direct light to the eyes from additional directions, e.g., top-left, top-right, bottom-left, bottom-right, etc.

Accordingly, the patient is directed to move his or her eyes to follow the alternately illuminated guide light sources 206 (i.e., up, down, to the left, to the right, and so on), thereby moving different areas of the eye, e.g., corneal surface, to the open area between the top and bottom eyelids. Even with blinking, substantially the entire surface of each eye is exposed between the top and bottom eyelids to the photoactivating light from the photoactivating light sources 204, and the photosensitizer in the treated tissue can be photoactivated for the antimicrobial effect. In this way, substantially the entire eye surface gets full coverage of irradiance without the need for specula to force the eyes wide open for the delivery of photoactivating light. The patient may sit up or lay down for the procedure for as long as necessary. Because the irradiance is low and the procedure lasts for an extended amount of time, irradiance variation is averaged and greatly minimized over time.

The body 202 also includes a battery 210 to power the photoactivating light sources 204, the guide light sources 206, and the controller 208. Initially, a plastic pull-tab can electrically separate the battery 210 from the other components. When the photoactivation device 200 is needed to deliver photoactivating light to the treated eyes, the pull-tab can be removed to connect the battery 210 with a conductive contact which delivers electrical power to the other components. Alternatively, the frame 202 may include an electrical switch that can be selectively operated to connect the battery 210 with the other components. The power from the battery 210 may be limited to what is necessary to operate the photoactivating light sources 204 and the guide light sources 206 to deliver the photoactivating light to the entire ocular surface with the desired low irradiance and desired extended irradiation time.

The end of the treatment may coincide with the depletion of power from the battery 210. Alternatively, the controller 208 may control the irradiation time. Alternatively, the components of the photoactivation device 200 may turn off (e.g., burn out) and self-destruct after a given amount of irradiation time.

Due to the configuration above, the photoactivation device 200 may be employed as a single-use, disposable device. The photoactivation device 200 does not include any lenses and can be inexpensively manufactured. For instance, the body 202 may be molded from plastic. Because photoactivation device 200 is not positioned too close to the eyes (e.g., the surgical field), the photoactivation device 200 should be clean but does not necessarily have to be sterile. Furthermore, the photoactivation device 200 might not be considered medical waste and as such may not require special disposal procedures.

The photoactivation device 200 may be configured to become inoperable once the treatment is complete. For instance, the battery 210 cannot be replaced once the power is depleted and the treatment is complete. Additionally or alternatively, as described above, the components of the photoactivation device 200 may self-destruct after a given amount of irradiation time.

In general, the photoactivation device 200 is more convenient and cost-effective than other irradiation systems. As such, the photoactivation device 200 may be more feasible for treatments in the third world and/or other remote locations.

The use of the photoactivation device 200 is not limited to humans. Indeed, the photoactivation device 200 can be especially modified/configured for treatment of animals, such as dogs, cats, horses, etc.

As described above, photochemical kinetic reactions can produce antimicrobial agents that place microbes in the tissue under stress and induce an apoptotic or necrotic response in the microbes. A description of photochemical kinetic reactions for riboflavin is provided, for example, in International Patent Application No. PCT/US15/57628, filed Oct. 27, 2015, the contents of which are incorporated entirely herein by reference. When riboflavin absorbs radiant energy, especially UVA light, it undergoes photoactivation. There are two photochemical kinetic pathways for riboflavin photoactivation, Type I and Type II. Some of the reactions involved in both the Type I and Type II mechanisms are as follows:

Common Reactions:

  (r1)

  (r2)

  (r3)

Type I Reactions:

  (r4)

  (r5)

Type II Reactions:

  (r6)

  (r7)

  (r8)

In the reactions described herein, Rf represents riboflavin in the ground state. $Rf^*_1$ represents riboflavin in the excited singlet state. $Rf^*_3$ represents riboflavin in a triplet excited state. $Rf^-$ is the reduced radical anion form of riboflavin. $RfH\cdot$ is the radical form of riboflavin. $RfH_2$ is the reduced form of riboflavin. DH is the substrate. $DH\cdot^+$ is the intermediate radical cation. $D\cdot$ is the radical. $D_{ox}$ is the oxidized form of the substrate.

Riboflavin is excited into its triplet excited state $Rf^*_3$ as shown in reactions (r1) to (r3). From the triplet excited state $Rf^*_3$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

$$Rf^*_3 \rightarrow Rf, \quad \kappa 8; \tag{r9}$$

$$Rf^*_3 + Rf \rightarrow 2RfH', \quad \kappa 9; \tag{r10}$$

$$RfH_2 + O_2 \rightarrow RfH' + H^+ + O_2^-, \quad \kappa 10; \tag{r11}$$

$$RfH' + O_2 \rightarrow Rf + H^+ + O_2^-, \quad \kappa 11; \tag{r12}$$

$$2 RfH_2 + O_2^- \rightarrow 2 RfH' + H_2O_2, \quad \kappa 12; \tag{r13}$$

$$2 RfH' + O_2^- \rightarrow 2 Rf + H_2O_2, \quad \kappa 13; \tag{r14}$$

$$RfH' + H_2O_2 \rightarrow OH' + Rf + H_2O, \quad \kappa 14; \tag{r15}$$

$$OH' + DH \rightarrow D' + H_2O, \quad \kappa 15; \tag{r16}$$

$$D' + D' \rightarrow D - D, \quad \kappa 16; \quad CXL \tag{r17}$$

$$O_2^1 \rightarrow O_2, \quad \kappa 18; \tag{r18}$$

$$D' + RfH_2 \rightarrow RfH' + DH, \quad \kappa 19; \tag{r19}$$

$$Rf + Rf \underset{\kappa_a^-}{\overset{\kappa_a^+}{\rightleftarrows}} A_1, \quad \kappa_a = \kappa_a^+ / \kappa_a^- \tag{r20}$$

$$RfH_2 + RfH_2 \underset{\kappa_a^-}{\overset{\kappa_a^+}{\rightleftarrows}} A_2, \quad \kappa_a = \kappa_a^+ / \kappa_a^- \tag{r21}$$

$$Rf + RfH_2 \underset{\kappa_b^-}{\overset{\kappa_b^+}{\rightleftarrows}} A_3, \tag{r22}$$

$$\kappa_b = \kappa_b^+ / \kappa_b^-$$

$$Rf^*_1 + A \rightarrow Rf + A, \quad \kappa_{1a} \tag{r23}$$

$$Rf^*_3 + A \rightarrow Rf + A, \quad \kappa_{3a} \tag{r24}$$

$$2 O_2^- \rightarrow O_2 + H_2O_2, \quad \kappa_{12} \tag{r25}$$

$$OH + CXL \rightarrow \text{insert products}, \quad \kappa_{OH} \tag{r26}$$

Figure 6:
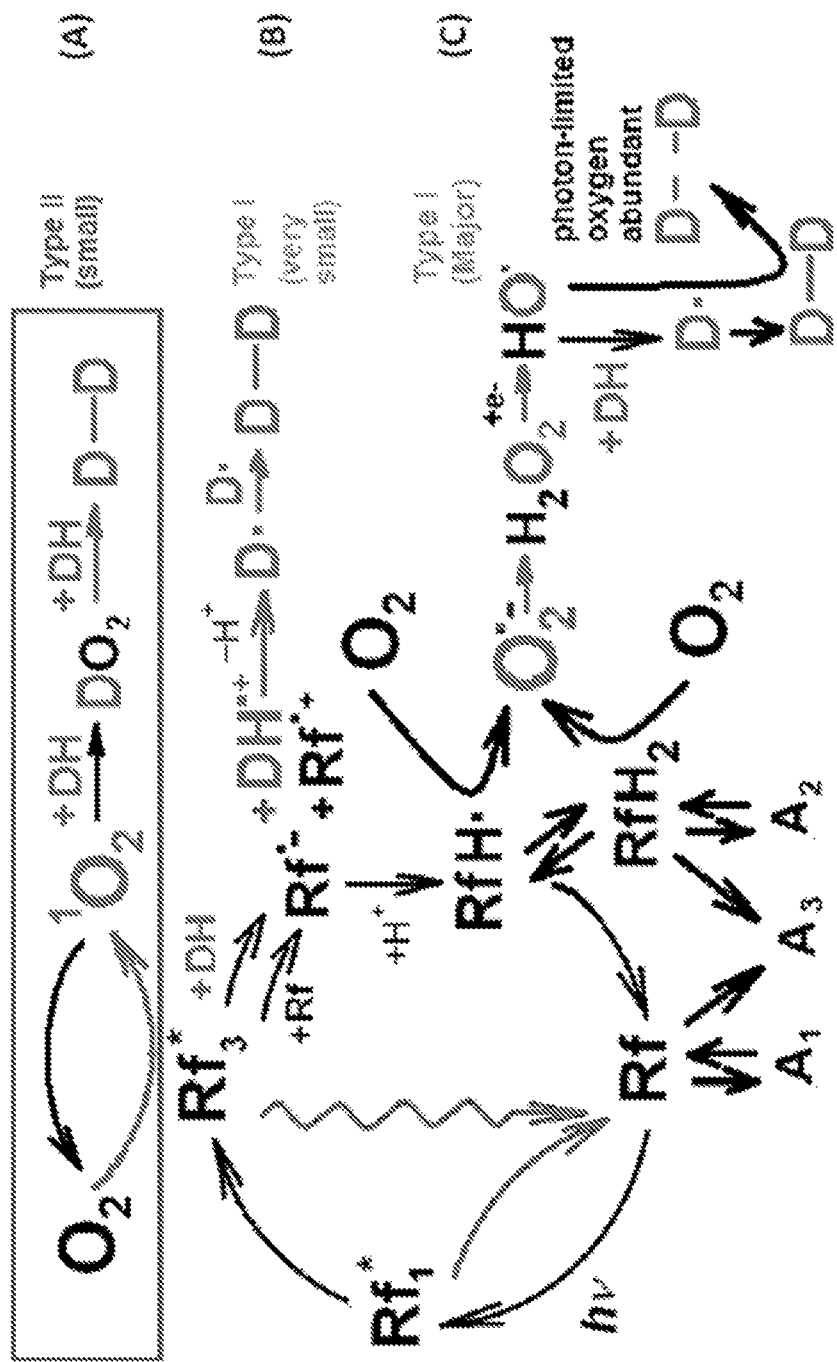
FIG. 6 illustrates a diagram for photochemical kinetic reactions involving riboflavin and UVA light applied during a corneal treatment, according to aspects of the present disclosure.

FIG. 6 illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals ($\cdot OH$) in reactions (r13) through (r17).

As shown in FIG. 6, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) may account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

Excess oxygen may be detrimental in corneal cross-linking process. As shown in FIG. 6, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

A large variety of factors as described herein affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for riboflavin treatment is provided by the photochemical kinetic reactions (r1)-(r26) identified above. Accordingly, systems and methods can adjust various parameters for photosensitizer treatment according to this photochemical kinetic model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but is not limited to: the concentration(s) and/or soak times of the applied photosensitizer; the dose(s), wavelength(s), irradiance(s), duration(s), and/or on/off duty cycle(s) of the photoactivating light; the oxygenation conditions in the tissue; and/or presence of additional agents and solutions.

As further described above, example embodiments can generate ROS at desired depths and at rates to achieve an antimicrobial effect throughout the thickness of the cornea while minimizing cross-linking of the anterior cornea. The photochemical kinetic reactions above can be employed to determine the threshold at which cross-linking activity is generated at depths within the cornea. Using a model based on the photochemical kinetic reactions, the example embodiments can be configured accordingly to generate ROS for the antimicrobial effect without reaching the determined threshold for cross-linking activity.

It is understood, however, that alternative embodiments may call for cross-linking activity (to modify biomechanical properties) in addition to antimicrobial treatment. As such, the model based on the photochemical kinetic reactions allows these alternative embodiments to generate ROS and/or other radicals for the desired antimicrobial effect and desired cross-linking activity.

In addition to the factors described above, example embodiments may enhance the photochemical kinetic reactions by adding a metal, such as iron or copper, to the riboflavin formulation. A description of how additives can affect photochemical kinetic reactions is provided, for example, in U.S. patent application Ser. No. 14/281,638, filed May 19, 2014 and titled "Systems, Methods, and Compositions for Cross-Linking" and U.S. Provisional Patent Application No. 62/086,572, filed Dec. 2, 2014 and also titled "Systems, Methods, and Compositions for Cross-Linking," the contents of these application being incorporated entirely herein by reference.

For instance, trace amounts of copper (ranging from approximately 0.1 mM to approximately 10 mM) can provide an enhanced antimicrobial effect for a riboflavin formulation. Copper can enhance the photodynamic effect of riboflavin through a Fenton-type reaction. Moreover, copper on its own (specifically, copper ions) can have an antimicrobial effect even when it is not combined with a photosensitizer. Therefore, the enhanced mode of action for a riboflavin formulation with a copper additive involves enhancement though the Fenton-type reaction and/or the antimicrobial effect of the copper by itself.

The photochemical kinetic reactions for a riboflavin formulation can be enhanced by adding a deuterated water ($D_2O$), also known as "heavy water." $D_2O$ by itself does not kill bacteria. Skladnev D. A., et al. Methylotrophic Bacteria as Sources of 2H- and 13C-amino Acids. Biotechnology (1996), pp. 14-22. However, $D_2O$ can increase the presence of singlet oxygen when used in combination with a photosensitizer formulation (and optionally other additives). Singlet oxygen is one of the ROS responsible for producing an antimicrobial effect through Type II photochemical kinetic energy transfer. Type II photochemical kinetic reactions are described, for example, in U.S. patent application Ser. No. 13/841,617 cited above. Thus, example embodiments may employ $D_2O$ to enhance the antimicrobial effect associated with singlet oxygen.

Example embodiments may also employ timed application of agents, such as dimethyl sulfoxide (DMSO), which can cause penetration of a photosensitizer to desired depths in the targeted tissue and produce an antimicrobial effect at the desired depths. In some cases, the antimicrobial effect at the desired depths may be further enhanced by increasing the oxygen concentration available for the photochemical reactions with the photosensitizer.

Example embodiments may also employ timed application of quenching agents to generate greater antimicrobial effect at the desired depths. The quenching agents can limit the photochemical reaction in regions closer to the surface of the tissue and allow the antimicrobial effect of the photosensitizer to take place deeper in the tissue. Quenching agents are described, for example, in U.S. patent application Ser. No. 13/475,175, filed May 18, 2012 and titled "Controlled Application of Cross-Linking Agent," the contents of which are incorporated entirely herein by reference.

Example embodiments may also increase or decrease the pH of the tissue to enhance the antimicrobial effect of antimicrobial treatments. The pH of the tissue may be modified by selectively applying acidic or basic solutions. In some cases, the acidic or basic solutions may include additives as described herein. For example, the solutions may include quenching agents to control the photochemical reactions at a given depth within the tissue.

Example embodiments may employ a dispensing device configured to apply different formulations and/or different concentrations according to a predetermined sequence. The dispensing device, for instance, may be a charged nanocloud device that applies the photosensitizer formulations via aerosolized electro-spraying. In some cases, the dispensing device may generate and deliver a dual payload of ionized ROS encapsulated in photosensitizer nanoparticles for simultaneous intra-stromal deposition.

Example embodiments may additionally employ water nanoparticles for antimicrobial applications. Electro-spraying ionized water ("engineered water") results in nanocaging ROS via an excess of electrons loaded during droplet fission thereby conferring the nanoparticles with antimicrobial properties.

Example embodiments may employ nanostructures to promote delivery of photosensitizer formulations to the target tissue and enhance the antimicrobial effect of the photochemical kinetic reactions. The nanostructures may include, but are not limited to, liposomes, polymeric micelles, ceramic (graphene oxide) and metallic nanorods. These nanostructures may be included in drops that are applied to the target tissue. Alternatively, specially configured structures may be employed to allow the nanostructures and photosensitizer formulations to penetrate the target tissue.

For instance, a contact lens device may be configured to allow different photosensitizer formulations and nanostructures to penetrate a cornea in a corneal procedure. The contact lens device may be applied to the cornea for several minutes or even a few hours before illumination is applied to initiate photochemical kinetic reactions. Such a device facilitates delivery through the epithelium for procedures that keep the epithelium in place, i.e., "epi-on" procedures.

In an example procedure, very low concentrations of drug formulation may be applied to eye tissue, followed by application of illumination at very low irradiance levels, e.g., a formulation with approximately 0.02% riboflavin concentration followed by approximately 1 mW/cm$^2$ illumination of UV light. The contact lens devices described above can be applied to the subject's eyes for 30-90 minutes to deliver the formulation. Once the contact lens devices are removed and the photoactivation device 100 is positioned over the subject's eyes to deliver the illumination to generate the photochemical kinetic reactions.

In view of the foregoing, example embodiments can enhance antimicrobial treatments by any combination of:
 employing different photosensitizer formulations at various concentrations;
 employing specialized additives with the photosensitizer formulation(s);
 controlling oxygen available to the photochemical reactions through hyperbaric, hyperoxic, and/or hypoxic conditions;
 employing time dependent quenching agents;
 manipulating temperature of the target tissue;
 manipulating the pH of the photosensitizers or additives;
 employing nanostructures;
 controlling the delivery of photosensitizer(s) to the tissue; and/or
 controlling the delivery of light to the target tissue treated with the photosensitizer formulation(s).

Although the example embodiments above involve treatments of the eye, it is understood that aspects of the present disclosure can be applied to treatments of other parts of the body. For instance, alternative applications such as Ventilator Associated Pneumonia (VAP) treatments can be addressed by the use of combinations of aerosolized drugs/photosensitizers and ionized ROS in water nanoparticles. These can be delivered to the oral and tracheal regions with targeted multi-drug resistant anti-bacterial payloads (MDR *A. baumannii, P. aeruginosa*). In an example VAP application, a pre-tracheal mouthpiece tube having actinic illumination targets ROS-photosensitizer nanoparticles flowing into the oral cavity.

The embodiments described herein may employ controllers and other devices for processing information and controlling aspects of the example systems. For example, the example photoactivation device 100 shown in FIGS. 1*a, b* includes the controller 116 or the photoactivation device 200 shown in FIG. 4 includes the controller 208. Generally, the controllers include one or more processors. The processor(s) of a controller or other devices may be implemented as a combination of hardware and software elements. The hardware elements may include combinations of operatively coupled hardware components, including microprocessors, memory, signal filters, electronic/electric chip/circuit, etc. The processors may be configured to perform operations specified by the software elements, e.g., computer-executable code stored on computer readable medium. The processors may be implemented in any device, system, or subsystem to provide functionality and operation according to the present disclosure. The processors may be implemented in any number of physical devices/machines. Indeed, parts of the processing of the example embodiments can be distributed over any combination of processors for better performance, reliability, cost, etc.

The physical devices/machines can be implemented by the preparation of integrated circuits or by interconnecting an appropriate network of conventional component circuits, as is appreciated by those skilled in the electrical art(s). The physical devices/machines, for example, may include field programmable gate arrays (FPGA's), application-specific integrated circuits (ASIC's), digital signal processors (DSP's), etc.

Appropriate software can be readily prepared by programmers of ordinary skill based on the teachings of the example embodiments, as is appreciated by those skilled in the software arts. Thus, the example embodiments are not limited to any specific combination of hardware circuitry and/or software. Stored on one computer readable medium or a combination of computer readable media, the computing systems may include software for controlling the devices and subsystems of the example embodiments, for driving the devices and subsystems of the example embodiments, for enabling the devices and subsystems of the example embodiments to interact with a human user (user interfaces, displays, controls), etc. Such software can include, but is not limited to, device drivers, operating systems, development tools, applications software, etc. A computer readable medium further can include the computer program product(s) for performing all or a portion of the processing performed by the example embodiments. Computer program products employed by the example embodiments can include any suitable interpretable or executable code mechanism, including but not limited to complete executable programs, interpretable programs, scripts, dynamic link libraries (DLLs), applets, etc. The processors may include, or be otherwise combined with, computer-readable media. Some forms of computer-readable media may include, for example, a hard disk, any other suitable magnetic medium, any suitable optical medium, RAM, PROM, EPROM, flash memory, any other suitable memory chip or cartridge, any other suitable non-volatile memory, a carrier wave, or any other suitable medium from which a computer can read.

The controllers and other devices may also include databases for storing data. Such databases may be stored on the computer readable media described above and may organize the data according to any appropriate approach. For example, the data may be stored in relational databases, navigational databases, flat files, lookup tables, etc.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method for antimicrobial treatment, comprising:
identifying an eye infected by a microbe;
applying a photosensitizer to the eye;
applying a photoactivation device to the eye, the photoactivation device including:
a body defining a chamber shaped to be positioned over the eye;
one or more photoactivating light sources coupled to the body; and
an inlet configured to couple the body to an oxygen source;
modifying oxygen conditions in the chamber by delivering oxygen from the oxygen source via the inlet; and
operating the one or more photoactivating light sources to deliver photoactivating light to the eye according to illumination parameters that determine a dose of the photoactivating light that activates the photosensitizer applied to the eye,
wherein activation of the photosensitizer provides an antimicrobial effect in the eye depending on the oxygen conditions including at least an oxygen concentration.

2. The method of claim 1, wherein identifying the eye infected by the microbe includes identifying keratitis in the eye.

3. The method of claim 1, wherein the one or more photoactivating light sources deliver the photoactivating light as at least one of pulses or continuous waves, and the illumination parameters include at least one of wavelength, power, irradiance, intensity, duration, or duty cycle.

4. The method of claim 1, wherein the dose of the photoactivating light activates the photosensitizer and provides the antimicrobial effect in the eye without inducing crosslinking activity that produces biomechanical changes in the eye.

5. The method of claim 1, wherein the activation of the photosensitizer generates reactive oxygen species that provide the antimicrobial effect.

6. The method of claim 1, further comprising generating, with one or more heating elements, heat in the chamber according to temperature parameters, the temperature parameters modifying the activation of the photosensitizer applied to the eye and the antimicrobial effect in the eye.

7. The method of claim 6, wherein the one or more heating elements are coupled to the body.

8. The method of claim 1, wherein the oxygen from the oxygen source modifies a temperature in the chamber according to temperature parameters, the temperature parameters modifying the activation of the photosensitizer applied to the eye and the antimicrobial effect in the eye.

9. The method of claim 1, further comprising applying one or more permeability enhancers to the eye.

10. The method of claim 9, wherein the one or more permeability enhancers enhance penetration of the photosensitizer into the eye.

11. The method of claim 9, wherein the one or more permeability enhancers enhance uptake of the photosensitizer by the microbe.

12. The method of claim 9, wherein the one or more permeability enhancers include non-ionic surfactants.

13. The method of claim 1, further comprising applying mechanical forces to the eye to enhance penetration of the photosensitizer into the eye.

14. The method of claim 1, wherein the photosensitizer includes riboflavin, and the one or more photoactivating light sources deliver ultraviolet light.

* * * * *